United States Patent
Markert et al.

(10) Patent No.: US 7,537,933 B2
(45) Date of Patent: May 26, 2009

(54) METHOD FOR DETERMINING THE ENANTIOMER RATIO TRIMETHYLCYCLOPENTENE DERIVATIVES

(75) Inventors: Thomas Markert, Monheim (DE); Armin Mosandl, Dettelbach (DE); Steffi Bilke, Ratingen (DE)

(73) Assignee: KAO Corporation, Tokyo (JP)

( * ) Notice: Subject to any disclaimer, the term of this patent is extended or adjusted under 35 U.S.C. 154(b) by 862 days.

(21) Appl. No.: 10/488,250

(22) PCT Filed: Sep. 3, 2002

(86) PCT No.: PCT/EP02/09827

§ 371 (c)(1),
(2), (4) Date: Sep. 7, 2004

(87) PCT Pub. No.: WO03/022784

PCT Pub. Date: Mar. 20, 2003

(65) Prior Publication Data

US 2005/0019938 A1 Jan. 27, 2005

(30) Foreign Application Priority Data

Sep. 12, 2001 (DE) ................. 101 44 888

(51) Int. Cl.
- G01N 33/00 (2006.01)
- C07B 57/00 (2006.01)
- C07C 35/06 (2006.01)
- C07C 35/00 (2006.01)

(52) U.S. Cl. .................... 436/139; 73/866; 435/803

(58) Field of Classification Search ................ 436/161; 512/8; 525/474; 568/838; 504/142; 546/133
See application file for complete search history.

(56) References Cited

U.S. PATENT DOCUMENTS

| | | | | |
|---|---|---|---|---|
| 5,403,898 | A * | 4/1995 | Bradshaw et al. ........... | 525/474 |
| 5,504,066 | A * | 4/1996 | Markert et al. ............. | 512/8 |
| 5,599,937 | A * | 2/1997 | Glas et al. ............... | 546/133 |
| 5,994,291 | A * | 11/1999 | Aida et al. ............... | 512/8 |
| 6,028,231 | A * | 2/2000 | Markert .................. | 568/838 |
| 6,310,003 | B1 * | 10/2001 | Gries et al. .............. | 504/142 |

FOREIGN PATENT DOCUMENTS

| EP | 0 829 463 | 3/1998 |
|---|---|---|
| EP | 0829463 | 3/1998 |
| EP | 0 841 318 | 5/1998 |
| EP | 0841318 | 5/1998 |
| EP | 0 997 534 | 5/2000 |
| EP | 0997534 | 5/2000 |
| EP | 1 031 629 | 8/2000 |
| EP | 1031629 | 8/2000 |

OTHER PUBLICATIONS

Klobes U. et al, Enantioseparation of the Compounds of Technical Toxaphene (CTTs) on 35% Heptakis(6-O-tert-Butyldimethylsilyl-2,3-di-O-Methyl)-beta-Cyclodextrin in OV1701, Chromatographia, vol. 47, No. 9-10, May 1998, pp. 565-569.*

Beck Thomas, et al, gamma-Dithiolactones-Analytical and Sensory Characteristics, J. High Resol. Chromatogr. 1999, 22, (7) 421-423.*

Reinhardt R et al: "Enantiomer separation of alpha-campholene and fencholene derivatives by capillary gas chromatography on permethylated cyclodextrin phases I. Compounds separable with single columns" Journal of Chromatography A, Elsevier Science, NL, Bd. 697, Nr. 1, 21. (Apr. 21, 1995), Seiten 475-484, XP004023082 ISSN: 0021-9673 in der Anmeldung erwaehnt das ganze Dokument.

Steinborn A et al: "Enantiomer separation of alpha-campholene and fencholene derivatives by capillary gas chromatography on permethylated cyclodextrins II. Compounds separable with coupled techniques" Journal of Chromatography A, Elsevier Science, NL, Bd. 697, Nr. 1, 21. (Apr. 21, 1995), Seiten 485-494, XP004023083 ISSN: 0021-9673 in der Anmeldung erwaehnt das ganze Dokument.

Reinhardt, R. et al. "Enantiomer separation of alpha-campholene and fencholene derivatives by capillary gas chromatograhpy on permethylated cyclodextrin phases I. Compounds separable with single columns", Journal of Chromatography A, vol. 697, pp. 475-484 1995.

Steinborn, A et al. "Enantiomer separation of alpha-campholene and fencholene derivatives by capillary gas chromatography on permethylated cyclodextrins II. Compounds separable with coupled techniques", Journal of Chromatography A, vol. 697, pp. 485-494 1995.

* cited by examiner

*Primary Examiner*—Walter D Griffin
*Assistant Examiner*—Christine T Mui
(74) *Attorney, Agent, or Firm*—Oblon, Spivak, McClelland, Maier & Neustadt, P.C.

(57) ABSTRACT

The invention relates to a method for determining the enantiomer ratio of trimethylcyclopentene derivatives of structure (I), wherein Z is an alkyl radical having 1-10 C atoms, can be saturated or olefinically unsaturated, straight-chained or branched and which is substituted by an OH or CHO group, by means of capillary gas chromatography, wherein a stationary phase is applied containing a compound selected from the group of Heptakis-(2,3-di-O-methyl-6-O-tert.-butyldimethylsily)-β-Cyclodextrin and Heptakis-(2,3-di-O-acetyl-6-O-tert.-butyldimethylsilyl)-β-Cyclodextrin and at least one polysiloxane, wherein the mixing ratio of Cyclodextrin derivatives and polysiloxanes is adjusted to a value ranging from 10:90 to 50:50.

12 Claims, No Drawings

METHOD FOR DETERMINING THE ENANTIOMER RATIO TRIMETHYLCYCLOPENTENE DERIVATIVES

FIELD OF THE INVENTION

The present invention relates to a method for determining the enantiomer ratio of sandalwood odoriferous materials, which structurally constitute trimethylcyclopentene derivatives.

PRIOR ART

Sandalwood odoriferous materials are an important class of odoriferous materials. A large number of these odoriferous materials is structurally characterized in that it contains a 4-(2,2,3-trimethylcyclopent-3-en)-1-yl residue as a joint structural element. This structural element is normally linked to an alkyl residue which may be saturated or olefinically unsaturated, straight-chain or branched and which contains an OH or CHO group. Said residue contains a chiral center, namely at C-1. This means that the corresponding sandalwood odoriferous materials can be present as a blend of enantiomers. Since often only one of the enantiomers is olfactorily valuable, a quick and reliable determination of the enantiomer ratio is of great importance in practice. However, no such determination has been known to date to the person skilled in the art in the technical field at issue here.

In this regard, the following should be noted: 2-methyl-4-(2,2,3-trimethylcyclopent-3-en-1-yl)-but-2-enol, which has a chiral center at the C-1 of the cyclopentene ring and which is commercially distributed by various manufacturers, constitutes a very important synthetic sandalwood odoriferous material; different opinions have been held in more recent technical publications as to the question of which enantiomer is responsible for the distinct sandalwood odor. Buchbauer et al. stated in 1997 that the (R)-(+) enantiomer has a sweet, rose-like scent, whereas the (S)-(−) enantiomer exhibits the typical sandalwood fragrance as well as animal notes [G. Buchbauer et al., Chiralty 1997, pp. 380-385]. On the other hand, Bajgrowicz et al. held the opinion in 1998 that the distinct sandalwood fragrance was to be attributed to the (R)-(+) enantiomer [J. Bajgrowicz et al. Helv. Chimica Acta 1998, pp. 1349-1358]. Bajgrowicz et al. pointed out themselves that contrasting structure-odor-correlations have been published in literature as regards 2-methyl-4-(2,2,3-trimethylcyclopent-3-en-1-yl)-but-2-enol, namely in the aforementioned publication of Buchbauer et al. and in EP-A-829 463.

Furthermore, Engewald et al. reported on the enantiomer separation of α-campholene derivatives by means of capillary gas chromatography using permethylated cyclodextrin phases [W. Engewald et al., Journal of Chromatography A, 1995, pp. 475-484 and pp. 485-494]. Their efforts to separate the enantiomers of 2-methyl-4-(3-ethyl-2,2-dimethylcyclopent-3-en-1-yl)-but-3-enal and 2-methyl-4-(3-ethyl-2,2-dimethylcyclopent-3-en-1-yl)-but-3-enol on permethylated cyclodextrin phases remained, however, unsuccessful. This should also be expected in view of the results cited above with regard to 2-methyl-4-(2,2,3-trimethylcyclopent-3-en-1-yl)-but-2-enol, since the tested substances are structurally very similar.

Cyclodextrins are cyclic oligomers consisting of α-1,4-linked glucopyranose units and have already been known since 1891. They are formed by microbial degradation of starch. A number of up to 12 glucose units can be attained thereby, however, those consisting of 6, 7 and 8 monomers (α-, β-, γ-cyclodextrin) have been studied best. All of these molecules form a kind of cone, the size of which depends on the number of glucose units. The primary hydroxy groups at C-6 form one edge of the cone, the secondary at C-2 and C3 form the second. Aliphatic CH-bonds prevail in the interior. This arrangement leads to a molecule having a hydrophilic outer edge and a lipophilic pocket. Since cyclodextrins are non-toxic and biodegradable, they have found use in many fields. Thus, lipophilic active ingredients of medicaments are encapsulated in cyclodextrins in order to improve absorption in the aqueous system of the body.

EP-A-1 031 629 describes a method for preparing stereoisomeric carboxylic acid esters. The determination of the absolute configuration and of the enantiomer and diastereomer excess is described in more detail in the experimental part. In accordance therewith, the enantiomer excess of the carboxylic acid esters was determined gas chromatographically by means of a heptakis(2,3-di-O-acetyl-6-O-TBDMS)-β-cyclodextrin column (25 m×0.25 mm, Prof. W. A. König, University of Hamburg). The enantiomer excess of the alcohol was determined by gas chromatography using a heptakis (2,3,6-tri-O-methyl)-β-cyclodextrin column (50 m×0.25 mm, CS-Chromatographie-Service, Langerwehe).

EP-A-997 534 describes a method for separating racemic mixtures of arylalkylcarboxylic acid esters. The chemical and optical purity of the compounds as compared to the racemate were proven and/or determined by means of NMR and GC analyses. The GC analyses were carried out by means of an OPTIMA 5 column (25 m×0.25 mm; Macherey & Nagel, Düren, Germany) to determine conversion and purity, and by means of a heptakis(2,3-di-O-acetyl-6-O-TBDMS)-β-cyclodextrin column (25 m×0.25 mm, Prof. W. A. König, University of Hamburg) to determine the enantiomer excess.

EP-A-829 463 describes butenols of the formula reproduced below:

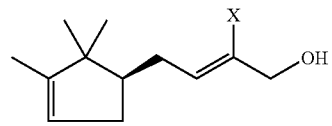

Therein, the residue X represents an alkyl group having 1 to 3 C atoms. These butenols are stated to be characterized by a distinct sandalwood fragrance. When acknowledging prior art, the aforementioned European patent application points out that attempts to gas chromatographically separate the enantiomers of 2-ethyl-4-(2,2,3-trimethylcyclopent-3-en-1-yl)-2-butenol-1 by using a chiral column (hereinafter also referred to as enantio-GC) have failed (cf. EP-A-829 463, p. 2, ls. 22-24).

DESCRIPTION OF THE INVENTION

The object of the present invention was to provide a method permitting quick and reliable determination of the enantiomer ratio of sandalwood odoriferous materials containing a (2,2,3-trimethylcyclopent-3-en-1-yl) residue as a joint structural element.

The subject matter of the present invention is a method for determining, by means of capillary gas chromatography, the enantiomer ratio of trimethylcyclopentene derivatives of structure (I),

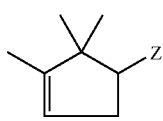

wherein Z represents an alkyl residue having 1 to 10 C atoms, which may be saturated or olefinically unsaturated, straight-chain or branched and which is substituted by an OH or a CHO group, with a stationary phase being used containing at least one compound selected from the group consisting of heptakis-(2,3-di-O-methyl-6-O-tert-butyldimethylsilyl)-β-cyclodextrin and heptakis-(2,3-di-O-acetyl-6-O-tert-butyldimethylsilyl)-β-cyclodextrin, and at least one polysiloxane, with the mixing ratio of cyclodextrin derivatives and polysiloxanes being set to a value in the range of 10:90 to 50:50.

It is expressly noted that it is surprising for the person skilled in the art that the aforementioned object is attained by the method according to the present invention. While it is known from the prior art as described above that special substances can be analytically characterized by using enantio-GC, it also belongs to general expert knowledge that such special results cannot be easily transferred to other substance classes without making an inventive contribution. This is also proven by the indication in EP-A-829 463, which has also been quoted previously, that attempts to separate the enantiomers of 2-ethyl-4-(2,2,3-trimethylcyclopent-3-en-1-yl)-2-buten-1-ol by means of enantio-GC have failed.

The preparation of the compounds (I) is known to the person skilled in the art and takes place according to synthesis methods of organic chemistry that are known per se. A synthetic pathway generally known for the important class of 4-(2,2,3-trimethylcyclopent-3-enyl)-but-2-en-1-ols, which may optionally be 2-alkyl-substituted and which constitute attractive sandalwood odoriferous materials, starts from α-campholene aldehyde and can be implemented in a mixed aldol condensation in the presence of common catalysts with corresponding short-chain aldehydes and ketones such as, for example, propionaldehyde, 2-butanone or 3-pentanone, with the corresponding α,β-unsaturated aldol condensation products being directly obtained via intermediary aldol condensation products by the elimination of water. The reaction is expediently carried out with an excess of the more reactive and more volatile components. For example, sodium hydroxide, sodium methanolate, sodium amide, potassium tert-butanolate or heterogeneous catalysts such as potassium fluoride on aluminum oxide come into consideration as catalysts. The carbonyl function of the aldol condensation products can be selectively reduced, in a further reaction, to the OH group, for example by using complex hydrides such as lithium aluminum hydride, or lithium and/or sodium borohydrate. It is likewise possible to reduce the CHO function of the aldol condensation products by means of hydrogen in the presence of Cu-Zn catalysts.

The stationary phase contains, in addition to the cyclodextrin derivatives to be used in accordance with the invention, at least one polysiloxane, with the mixing ratio of cyclodextrin derivatives and polysiloxanes being set to a value in the range of 10:90 to 50:50. For the purposes of the present invention, the mixing ratios always mean weight ratios.

The ranges of 20:80 to 50:50 and in particular 30:70 to 50:50 are particularly preferred thereby.

"SE 52" and "OV 1701-vi" constitute especially suitable polysiloxanes. These substances are known to the person skilled in the art (SE 52 consists of 5% of diphenyl polysiloxane and of 95% of dimethyl polysiloxane; OV 1701-vi consists of 14% of cyanopropylphenyl polysiloxane and of 86% of dimethyl polysiloxane) and are commercially available.

The following stationary phases have proven to be particularly suitable for attaining the object according to the invention:

mixtures of (2,3-di-O-methyl-6-O-TBDMS)-β-CD and SE 52, mixtures of (2,3-di-O-acetyl-6-O-TBDMS)-β-CD and OV 1701-vi.

The layer thickness of the stationary phase in the GC capillary is not critical per se and is set in particular to values in the range of 0.15 μm to 0.35 μm. Values of approx. 0.25 μm are particularly preferred.

Preferably, a gas is used as carrier gas which is inert vis-à-vis the sandalwood odoriferous material to be determined of structure (I). For example, hydrogen, helium, nitrogen are suitable. The flow rate is not critical per se. It is set in particular to values in the range of 1 to 5 ml/min.

The length of the capillary column is not critical per se and is preferably selected in the range of 20 to 100 m and in particular approx. 30 m.

The inner diameter of the capillary column is not critical per se and is set in particular to values in the range of 0.1 to 0.53 mm. Values in the range of 0.2 to 0.3 mm are particularly preferred.

The material of the capillary columns is not critical per se, however, Duran glass or fused silica columns are preferably used.

The column temperature is preferably set to values in the range of 20 to 400° C. It is particularly advantageous thereby to run a temperature program. This is particularly important if it is to be ensured that not only a partial separation of the enantiomers occurs to a greater or lesser extent but that a good separation—the person skilled in the art speaks in this context of a "base line separation"—is reliably achieved.

The cyclodextrin derivatives to be used according to the invention are known to the person skilled in the art. They are characterized by the following structure:

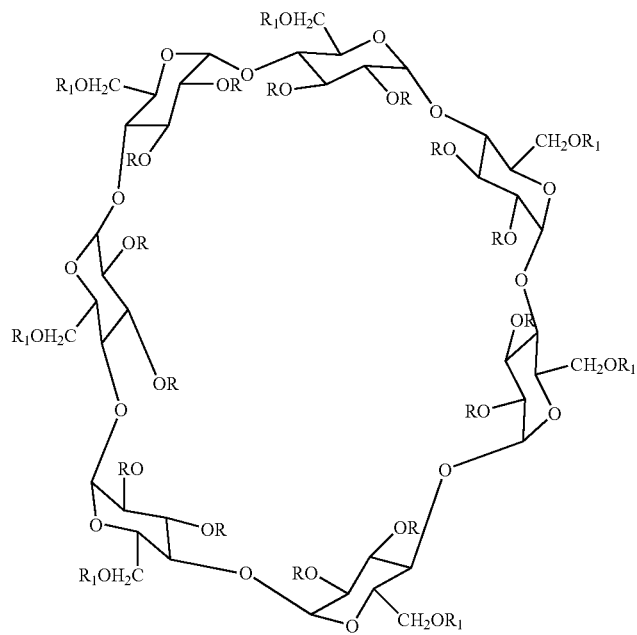

Therein, the residue $R_1$ represents a tert-butyldimethylsilyl group, and the residue R represents a methyl or acetyl group. It can be easily seen that if R=methyl the derivative is heptakis(2,3-di-O-methyl-6-O-tert-butyldimethylsilyl)-β-cyclodextrin, and if R=acetyl the derivative is heptakis(2,3-di-O-acetyl-6-O-tert-butyldimethylsilyl)-β-cyclodextrin. These two substances will hereinafter also be referred to in short as (2,3-di-O-methyl-6-O-TBDMS)-β-CD and (2,3-di-O-acetyl-6-O-TBDMS)-β-CD.

The following temperature program has proven to be particularly advantageous, and leads to a reliable base line separation for the determination of the enantiomer ratio of 2-methyl-4-(2,2,3-trimethylcyclopent-3-en-1-yl)-but-2-en-1-ol(I-a),

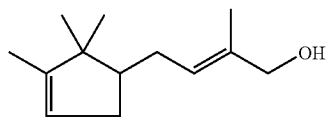
(I-a)

with (2,3-di-O-acetyl-6-O-TBDMS)-β-CD in OV 1701-vi being used as stationary phase: The initial temperature of 40° C. is maintained for 5 minutes, then heating occurs with 20° C./min to 80° C., this temperature is maintained for 200 minutes, then heating occurs with 0.5° C./min to 150° C. Numerous tests have shown that considerably worse or unusable results are obtained with temperature programs differing herefrom.

The following temperature program has proven to be particularly advantageous, and leads to a reliable base line separation for the determination of the enantiomer ratio of 2-methyl-4-(2,2,3-trimethylcyclopent-3-en-1-yl)-but-2-en-1-al (I-b),

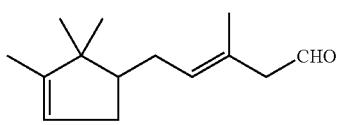
(I-b)

with (2,3-di-O-acetyl-6-O-TBDMS)-β-CD in OV 1701-vi being used as stationary phase: The initial temperature of 60° C. is maintained for 5 minutes, then heating occurs at a heating rate of 2° C./min to 210° C., and this temperature is maintained for 10 minutes.

The following temperature program has proven to be particularly suitable, and leads to a reliable base line separation for the determination of the enantiomer ratio of alpha-campholene aldehyde (I-c),

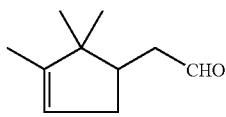
(I-c)

with (2,3-di-O-methyl-6-O-TBDMS)-β-CD in SE 52 being used as stationary phase: The initial temperature of 60° C. is maintained for 5 minutes, then heating occurs at a heating rate of 2° C./min to 210° C., and this temperature is maintained for 10 minutes.

The preparation of the capillary columns to be used according to the invention comprises several steps and occurs preferably as follows: (1) high-temperature silylation (surface deactivation): Different silanes are used individually or as a blend as silylation agents. Use is made in particular of phenyldimethylsilane; silylation occurs thereby with the following temperature program: 200° C. initial temperature, at a heating rate of 2° C./min to 400° C. (with glass columns) or 380° C. (with fused silica columns), the final temperature is maintained for 12 hours. Following silylation, the silylation agent is removed by rinsing the acid with different solvents; (2) load: filling the column with the load with a solvent mixture (cyclodextrin derivative and polysiloxane in dichloromethane/pentane 1:1), evaporation of the solvent. Especially if glass columns (i.e. not fused silica columns) are used, the aforementioned steps are preceded by the following procedure: (0-a) leaching (removal of metal ions from the glass surface): filling the column with 18% hydrochloric acid, heating to 180° C. for 15 hours; (0-b) rinsing (to remove the leached-out metal ions): rinsing with 1% hydrochloric acid; (0-c) dehydration: drying for 2 hours at 280° C.

The method in accordance with the invention is particularly suitable for determining the enantiomer ratio of the following compounds:

2-methyl-4-(2,2,3-trimethylcyclopent-3-en-1-yl)-but-2-en-1-ol (I-a)

2-methyl-4-(2,2,3-trimethylcyclopent-3-en-1-yl)-but-2-en-1-al (I-b)

α-campholene aldehyde (I-c)

The determination of the enantiomer ratio of 2-methyl-4-(2,2,3-trimethylcyclopent-3-en-1-yl)-but-2-en-1-ol (I-a) is especially preferred thereby.

EXAMPLES

Example 1

Determination of the Enantiomer Ratio of Campholene Aldehyde:

The enantioselective capillary gas chromatography of commercially available campholene aldehyde (substance produced by Glidco) was carried out on a Fisons Instruments GC 8000 gas chromatograph, equipped with a split/splitless injector and a flame ionization detector (carrier gas: H₂, column head pressure: 95 kPa; injector temperature: 240° C.; split flow: 30 mL/min; detector temperature: 250° C.). Separation was achieved by means of a 30 m×0.23 mm id Duran glass column loaded with a stationary phase of 30 wt. % of heptakis(2,3-di-O-methyl-6-O-tert-butyldimethylsilyl)-β-cyclodextrin and 70 wt. % of SE 52 (film thickness: 0.23 μm). The temperature program was as follows: isothermal for 5 min at 60° C., at a heating rate of 2° C./min to a final temperature of 210° C., this was maintained for 10 min.

Retention times: (S)-α-campholene aldehyde (26.5 min)
(R)-α-campholene aldehyde (26.9 min)

Example 2

Determination of the Enantiomer Ratio of 2-methyl-4-(2,2,3-trimethylcyclopent-3-en-1-yl)-but-2-enal:

The enantioselective capillary gas chromatography of 2-methyl-4-(2,2,3-trimethylcyclopent-3-en-1-yl)-but-2-enal, which was prepared from commercially available campholene aldehyde according to example 1 by condensation with propionaldehyde, was carried out on a Fisons Instruments GC 8000 gas chromatograph, equipped with a split/splitless injector and a flame ionization detector (carrier gas: H₂, column head pressure: 95 kPa; injector temperature: 240° C.; split flow: 30 mL/min; detector temperature: 250° C.). Separation was achieved by means of a 30 m×0.23 mm id Duran glass column loaded with a stationary phase of 50 wt. % of heptakis(2,3-di-O-acetyl-6-O-tert-butyldimethylsilyl)-β-cyclodextrin and 50 wt. % of OV 1701-vi (film thickness: 0.23 μm). The temperature program was as follows: isothermal for 5 min at 60° C., at a heating rate of 2° C./min to a final temperature of 210° C., this was maintained for 10 min.

Retention Times:
(S)-2-methyl-4-(2,2,3-trimethylcyclopent-3-en-1-yl)-but-2-enal (51.6 min)
(R)-2-methyl-4-(2,2,3-trimethylcyclopent-3-en-1-yl)-but-2-enal (51.8 min)

Example 3

Determination of the Enantiomer Ratio of 2-methyl-4-(2,2,3-trimethylcyclopent-3-en-1-yl)-but-2-enol:

The enantioselective capillary gas chromatography of 2-methyl-4-(2,2,3-trimethylcyclopent-3-en-1-yl)-but-2-enol, which was prepared by way of selective reduction of the aldehyde precursor according to example 2, was carried out on a Fisons Instruments GC 8000 gas chromatograph, equipped with a split/splitless injector and a flame ionization detector (carrier gas: H₂, column head pressure: 95 kPa; injector temperature: 240° C.; split flow: 30 mL/min; detector temperature: 250° C.). Separation was achieved using a 30 m×0.23 mm id Duran glass column loaded with a stationary phase of 50 wt. % of heptakis(2,3-di-O-acetyl-6-O-tert-butyldimethylsilyl)-β-cyclodextrin and 50 wt. % of OV 1701-vi (film thickness: 0.23 μm).

Temperature program: isothermal at 40° C. for 5 min, at a heating rate of 20° C./min to 80° C., after a further isothermal step for 200 min, at a heating rate of 0.5° C./min to a final temperature of 150° C.

Retention Times:
(S)-2-methyl-4-(2,2,3-trimethylcyclopent-3-en-1-yl)-but-2-enol (259.7 min)
(R)-2-methyl-4-(2,2,3-trimethylcyclopent-3-en-1-yl)-but-2-enol (261.1 min)

The invention claimed is:

1. A method for determining, by means of capillary gas chromatography, the enantiomer ratio of trimethylcyclopentene derivatives of structure (I),

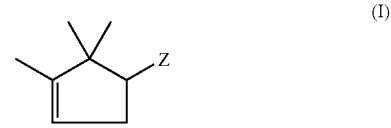

(I)

wherein Z represents an alkyl residue having 1 to 10 C atoms, which may be saturated or olefinically unsaturated, straight-chain or branched and which is substituted by an OH or CHO group, with a stationary phase being used containing at least one compound selected from the group consisting of heptakis-(2,3-di-O-methyl-6-O-tert-butyldimethylsilyl)-β-cyclodextrin and heptakis-(2,3-di-O-acetyl-6-O-tert-butyldimethylsilyl)-β-cyclodextrin, and at least one polysiloxane, with the mixing ratio of cyclodextrin derivatives and polysiloxanes being set to a value in the range of 10:90 to 50:50.

2. The method according to claim 1, with the mixing ratio of cyclodextrin derivatives and polysiloxanes being set to a value in the range of 30:70 to 50:50.

3. The method according to claim 1, with compound (I) being 2-methyl-4-(2,2,3-trimethylcyclopent-3-en-1-yl)-but-2-en-1-ol.

4. The method according to claim 1, with compound (I) being 2-methyl-4-(2,2,3-trimethylcyclopent-3-en-1-yl)-but-2-en-1-al.

5. The method according to claim 1, with compound (I) being alpha-campholene aldehyde.

6. The method according to claim 3, with heptakis-(2,3-di-O-acetyl-6-O-tert-butyldimethylsilyl)-β-cyclodextrin in OV 1701-vi being used as stationary phase.

7. The method according to claim 5, with heptakis-(2,3-di-O-acetyl-6-O-tert-butyldimethylsilyl)-β-cyclodextrin in SE 52 being used as stationary phase.

8. The method according to claim 3, with heptakis-(2,3-di-O-acetyl-6-O-tert-butyldimethylsilyl)-β-cyclodextrin in OV 1701-vi being used as stationary phase, and with the following temperature program being run when carrying out the chromatography: maintaining the initial temperature of 40° C. for 5 minutes, then heating with 20° C./min to 80° C., then maintaining this temperature for 200 minutes, subsequently heating with 0.5° C./min to 150° C.

9. The method according to claim 2, with compound (I) being 2-methyl-4-(2,2,3-trimethylcyclopent-3-en-1-yl)-but-2-en-1-ol.

10. The method according to claim 2, with compound (I) being 2-methyl-4-(2,2,3-trimethylcyclopent-3-en-1-yl)-but-2-en-1-al.

11. The method according to claim 2, with compound (I) being alpha-campholene aldehyde.

12. The method according to claim 4, with heptakis-(2,3-di-O-acetyl-6-O-tert-butyldimethylsilyl)-β-cyclodextrin in OV 1701-vi being used as stationary phase.

* * * * *